(12) United States Patent
Remon et al.

(10) Patent No.: US 10,251,866 B2
(45) Date of Patent: Apr. 9, 2019

(54) PHARMACEUTICAL NANOSUSPENSION

(71) Applicant: Universiteit Gent, Ghent (BE)

(72) Inventors: Jean Paul Remon, Melle (BE); Chris Vervaet, Kachtem (BE)

(73) Assignee: Universiteit Gent, Ghent (BE)

( * ) Notice: Subject to any disclaimer, the term of this patent is extended or adjusted under 35 U.S.C. 154(b) by 256 days.

(21) Appl. No.: 14/352,154

(22) PCT Filed: Oct. 18, 2012

(86) PCT No.: PCT/EP2012/070617
§ 371 (c)(1),
(2) Date: Apr. 16, 2014

(87) PCT Pub. No.: WO2013/057169
PCT Pub. Date: Apr. 25, 2013

(65) Prior Publication Data
US 2014/0255498 A1    Sep. 11, 2014

(30) Foreign Application Priority Data

Oct. 19, 2011    (EP) .................................... 11185803

(51) Int. Cl.
| A61K 9/10 | (2006.01) |
| A61K 9/14 | (2006.01) |
| A61K 47/12 | (2006.01) |
| A61K 47/26 | (2006.01) |
| A61K 31/4184 | (2006.01) |

(52) U.S. Cl.
CPC ............ *A61K 31/4184* (2013.01); *A61K 9/10* (2013.01); *A61K 9/14* (2013.01); *A61K 9/145* (2013.01); *A61K 47/12* (2013.01); *A61K 47/26* (2013.01)

(58) Field of Classification Search
None
See application file for complete search history.

(56) References Cited

U.S. PATENT DOCUMENTS

| 5,145,684 | A | * | 9/1992 | Liversidge | ............. | A61K 9/145 |
| | | | | | | 424/489 |
| 5,932,544 | A | | 8/1999 | Grinna | | |
| 2007/0293674 | A1 | * | 12/2007 | Scoppettuolo | ....... | A61K 31/496 |
| | | | | | | 544/366 |
| 2008/0194694 | A1 | * | 8/2008 | Comlay et al. | ............... | 514/618 |

| 2008/0213383 | A1 | | 9/2008 | Yamaguchi et al. | | |
| 2010/0092563 | A1 | * | 4/2010 | Raffaele | .................. | A61K 9/143 |
| | | | | | | 424/489 |
| 2010/0204204 | A1 | * | 8/2010 | Zaworotko | ............ | A61K 31/20 |
| | | | | | | 514/212.03 |

FOREIGN PATENT DOCUMENTS

| EP | 1923051 A1 | 5/2008 |
| WO | 03097012 A1 | 11/2003 |
| WO | 2004078163 A2 | 9/2004 |
| WO | 2010080754 A2 | 7/2010 |
| WO | 2011036676 A2 | 3/2011 |

OTHER PUBLICATIONS

Muller et al., "Nanosuspensions for the formulation of poorly soluble drugs I. Preparation by a size-reduction technique", 1998, vol. 160, pp. 229-237.*
Chen et al., "Nanonization strategies for poorly water-soluble drugs" Drug Discovery Today, vol. 16, Nos. 7/8, Apr. 2011, pp. 354-360.
Takatsuka et al., "Nanosizing of Poorly Water Soluble Compounds Using Rotation/Revolution Mixer", Chem. Pharm. Bull., Tokyo, 57(10), Oct. 2009, pp. 1061-1067.
Alhalaweh et al., "Preparation of Zolmitriptan-chitosan microparticles by spray drying for nasal delivery", European Journal of Pharmaceutical Sciences 38, 2009, pp. 206-214.
International Search Report and Written Opinion completed Nov. 16, 2012 pertaining to International Application No. PCT/EP2012070617 filed Oct. 18, 2012.
Extended European Search Report completed Mar. 6, 2012 pertaining to International Application No. EP11185803.1 filed Oct. 19, 2011.
The Merck Index: An Encyclopedia of Chemicals, Drugs, and Biologicals, 14th Edition, Merek Index Excerpt, https://www.amazon.com/Merck-Index-Encyclopedia-Chemicals-Biologicals/dp/091191000X/ref=sr_1_1?s=books&ie=UTF8&qid=1469027937&sr=1-1&keywords=merck+index+14th+edition, p. 1169.
David H. Bergstrom, et al.; Capsules, Soft; Encyclopedia of Pharmaceutical Technology; 2002; pp. 317-319; Marcel Dekker, Inc.

* cited by examiner

*Primary Examiner* — Robert A Wax
*Assistant Examiner* — Randeep Singh
(74) *Attorney, Agent, or Firm* — Dinsmore & Shohl LLP

(57) ABSTRACT

The present invention in general relates to a pharmaceutical suspension comprising nano-sized cocrystals of at least one active ingredient and at least one dicarboxylic acid. It in particular relates to a pharmaceutical suspension comprising nano-sized cocrystals of at least one anthelmintic drug and at least one dicarboxylic acid. The invention further relates to uses, methods for use and methods for manufacturing the pharmaceutical suspension according to this invention.

4 Claims, No Drawings

PHARMACEUTICAL NANOSUSPENSION

FIELD OF THE INVENTION

The present invention in general relates to a pharmaceutical suspension comprising nano-sized cocrystals of at least one active ingredient and at least one dicarboxylic acid. It in particular relates to a pharmaceutical suspension comprising nano-sized cocrystals of at least one anthelmintic drug and at least one dicarboxylic acid. The invention further relates to uses, methods for use and methods for manufacturing the pharmaceutical suspension according to this invention.

BACKGROUND TO THE INVENTION

A common technical problem associated with many drugs is their poor water solubility. Approximately 40% of potentially new drugs identified by pharmaceutical companies are poorly soluble in water, greatly hindering their further development. Furthermore, for specific application areas such as administration of drugs via drinking water, the poor water solubility of drugs is a major obstacle. In addition, low water solubility greatly limits the bioavailability and absorption of these agents. Therefore, technologies aimed at improving the dissolution profile of drugs are continuously being developed.

Recently, various nanonization strategies have emerged to increase the dissolution rate and bioavailability of numerous drugs that are poorly soluble in water and during the past decade, several drug nanoformulations have been clinically approved or are under clinical investigation (see review of Chen et al., 2011 below). Major research efforts have been focused on the development of enabling nanoformulation technologies to improve product properties, while keeping production costs as low as possible. Important parameters for providing a suitable nanoformulation include:

- minimizing the particle size, in order to obtain the highest possible solubility and dissolution rate.
- improving the stability of the particles, in particular for the manufacturing of a nanosuspension
- keeping production costs as low as possible
- improving the bioavailability, . . . .

Nanoformulations exist in various forms such as for example nanocrystals, nanoemulsions, and polymeric micelles. Nanocrystals are nano-sized crystals of the drug compound having dimensions generally less than 1 µm. It is common knowledge that the smaller the particle size, the higher the effective surface area, thereby resulting in an increased dissolution rate of the drug. Various methods exist for the preparation of nanocrystals such as nanoprecipitation, high-pressure homogenization and milling. The procedure making use of milling generally exists in charging a milling chamber with milling beads, dispersion media (e.g. water), drug powders and stabilizers. Subsequently, the beads are rotated at very high speed to generate strong shear forces to disintegrate drug powders into nanoparticles. Not only dry milling techniques exist, but also wet milling procedures have been developed making use of zirconium beads (Takatsuka, T. et al. (2009) Nanonizing of poorly soluble compounds using rotation/revolution mixer. Chem. Pharm. Bull. (Tokyo) 57, 1061-1067).

Exemplary nanoformulations of water-insoluble drugs that are approved for clinical use or that are still in clinical trials, prepared by milling techniques are represented in table 1.

TABLE 1

Available nanoformulations prepared by milling techniques (Chen et al., Drug Discovery Today Volume 16 Issues 7-8, April 2011, pages 654-360)

| Tradename | Drug | Other ingredients | Dosage Form |
|---|---|---|---|
| Rapamune ® | Sirolimus | PVP, poloxamer 188 | Oral Tablet |
| Emend ® | Eprepitant | HPC, SDS | Oral Capsule |
| Tricor ® | Fenofibrate | HPMC, SDS, Crospovidone | Oral Tablet |
| Megace ES ® | Megestrol | HPMC, Docusate Sodium | Oral Suspension |
| Invega ® | Paliperidone | Tween 20, PEG 4000 | Intramuscular suspension |

PVP: polyvinylpyrrolidone, HPC: Hydroxypropyl cellulose, SDS: sodium dodecyl sulphate, HPMC: Hydroxypropyl methylcellulose, PEG: polyethylene glycol Although the conventional nanonization procedures often result in increased solubility of the drug, there is a continuous need for further improvements to obtain better solubility rates for poorly soluble drugs. As evident from table 1, various additional ingredients have been added to the currently developed nanoformulations in order to obtain the best possible formulations. All of these compositions comprise at least one (co)polymer such as PVP, HPC, HPMC, PEG 4000 and Poloxamer; and most of them further comprises a surfactant such as SDS, Docusate and Tween 20. Also US20080213383 provides pharmaceutical nanoparticles comprising (co)polymers such as HPMC acetate succinate and HPMC phthalate.

We have now surprisingly found that a wet milling process not making use of (co)polymers but dicarboxylic acids and a surfactant instead results in a stable suspension of drugs comprising cocrystals having a particle size in the nanometer range.

WO2004078163 provides a co-crystal composition comprising an API and a co-crystal former, wherein the API and co-crystal former are hydrogen bonded to each other. Furthermore, although this patent application provides exhausting lists of API's and co-crystal formers, none of the few exemplified formulations were prepared by a nanonization method. Therefore a person skilled in the art, taken the teaching of this patent application, does not have indications that any of the disclosed co-crystal formers, let it be which one of them, could be used for optimizing a nanonization procedure.

WO2011036676 provides pharmaceutical cocrystals of temozolomide with co-crystal formers selected from aliphatic and aromatic carboxylic acids, including dicarboxylic acids. However, again no nanoparticle formulations are provided, and as such no teaching with regard to the use of co-crystal formers for optimizing a nanonization procedure are contained therein.

Cocrystal formation of drugs making use of dicarboxylic acids has been investigated by making use of spray drying and solvent evaporation methods (Alhalaweh A, et al. Preparation of zolmitriptan-chitosan microparticles by spray-drying for nasal delivery. 2010 Eur J Pharm Sci. 209; 38; 206-214). However, again the obtained co-crystals are far from nano-meter range having a size over 5 µm as evident from FIG. 1 of Alhalaweh et al., 2010. So no teaching with regard to the use of co-crystal formers for optimizing a nanonization procedure are disclosed therein.

WO2010080754 provides a pharmaceutical composition comprising nanoparticles comprising at least one aqueous-insoluble compound and at least one bile acid compound, wherein the aqueous-insoluble compound represents at least 76% of the total weight of aqueous-insoluble compound and bile acid compound in said nanoparticles. The exemplified formulations were all prepared by the solvent/anti-solvent process (bottom-up method) for nanonization. In this process the aqueous-insoluble compound(s) was first dissolved in an organic solvent, in particular ethanol, and subsequently mixed with an aqueous solution comprising the bile acid. However, in view of its use in the preparation of a medicament, one would like to reduce the use of organic solvents to a minimum. In preparing the formulations of the present invention, via milling (top-down method), no organic solvents need to be used, only aqueous suspensions are applied. Another disadvantage of the compositions described in WO2010080754 is the manufacturing price, as it is generally known that bile acid compounds are about 10-50× more expensive compared to dicarboxylic acids. Furthermore, cocrystal formation of drugs making use of dicarboxylic acids according to the present invention results in drugs comprising cocrystals having a particle size in the nanometer range as well as an improved stability in suspension.

SUMMARY OF THE INVENTION

In a first aspect, the present invention provides a pharmaceutical suspension comprising a surfactant and nano-sized cocrystals of at least one active ingredient and at least one dicarboxylic acid.

It in particular provides a pharmaceutical suspension comprising a surfactant and nano-sized cocrystals of at least one poorly water-soluble drug, in particular an anthelmintic such as a benzimidazole based anthelmintic; and at least one dicarboxylic acid.

In a specific embodiment, the present invention provides a pharmaceutical suspension according to this invention, wherein the benzimidazole based anthelmintic is selected from the list comprising albendazole, mebendazole, oxfendazole, febantel, thiabendazole, fenbendazole, triclabendazole and flubendazole; in particular flubendazole.

In another specific embodiment, the present invention provides a pharmaceutical suspension according to this invention, wherein the dicarboxylic acid is selected from the list comprising oxalic acid, malonic acid, succinic acid, glutaric acid, adipic acid, pimelic acid, suberic acid, azelaic acid, sebacic acid, undecanedioic acid, dodecanedioic acid, phtalic acid, isophtalic acid, terephthalic acid, maleic acic, fumaric acid, glutaconic acid, traumatic acid and muconic acid; in particular adipic acid.

In another specific embodiment, the present invention provides a pharmaceutical suspension according to this invention, wherein the surfactant is a non-ionic surfactant preferably selected from the list comprising SDS (sodium dodecyl sulphate), docusate, poloxamers, Triton X-100, Tween 20, Tween 80; and more preferred Tween 80.

In a preferred embodiment, the present invention provides a pharmaceutical suspension according to this invention comprising nano-sized cocrystals of flubendazole and adipic acid.

In a further aspect, the present invention provides a pharmaceutical composition obtained by drying the pharmaceutical suspension according to this invention.

In yet a further aspect, the present invention provides a pharmaceutical suspension or a pharmaceutical composition according to this invention for use as a human or veterinary medicine; in particular for the treatment of parasitic infections in a subject in need thereof, such as for example humans, pigs, poultry, cattle, sheep; in particular human, pigs and poultry.

In yet a further aspect, the present invention provides the use of one or more dicarboxylic acids for the manufacturing of a pharmaceutical suspension or a pharmaceutical composition according to this invention.

In yet a further aspect, the present invention provides a method for the treatment of parasitic infections; said method comprising administering a pharmaceutical suspension or a pharmaceutical composition according to this invention to a subject in need thereof, such as for example humans, pigs, poultry, cattle, sheep; in particular human, pigs and poultry.

In a further aspect, the present invention provides a method for the manufacturing of a pharmaceutical suspension according to this invention; said method comprising:
Dispersing at least one active ingredient, at least one dicarboxylic acid, and a surfactant in water, and
Milling said dispersion.

In a final aspect, the present invention provides a method for the manufacturing of a pharmaceutical composition according to this invention; said method comprising:
Dispersing at least one active ingredient, at least one dicarboxylic acid, and a surfactant in water,
Milling said dispersion, and
Drying the pharmaceutical suspension.

DETAILED DESCRIPTION OF THE INVENTION

In a first aspect, the present invention provides a pharmaceutical suspension comprising a surfactant and nano-sized cocrystals of at least one active ingredient and at least one dicarboxylic acid.

The present inventors unexpectedly have discovered that the addition of dicarboxylic acids during a nanonization procedure significantly reduces the obtained particle size. Furthermore, the obtained nanosuspensions are stable for at least 12, more particular at least 24 h, making them very suitable for administration of poor water-soluble drugs through drinking water of for example live stock. In addition, due to the optimization of the nanonizaton process by using dicarboxylic acids, the complete nanonization procedure can be performed without the addition of organic solvents, making the obtained formulations and compositions more interesting with regard to regulatory prescriptions.

As used herein, a 'pharmaceutical suspension' is meant to be a two-phase system consisting of a dispersed phase consisting of nano-sized particles; and an aqueous continuous phase.

The terms "nanoparticle(s)" and "nano-sized co-crystal(s)" refers to particles produced by the methods of this invention that in general have an average diameter of <1 µm, in particular between and about 100-800 nm, more particular between and about 100-500 nm, in particular between and about 100-350 nm, more in particular about 200 nm. The average diameter of a nanoparticle may be determined as the "average effective particle diameter", which may be measured by e.g. dynamic light scattering methods, or microscopy.

The term "co-crystal" as used herein is meant to be a crystalline structure made up of two or more components interacting with each other via non-covalent interactions such as hydrogen bonding, ionic interactions, and van der Waals interactions. Multiple techniques for preparing co-crystals exist, and may be used in preparing the solutions and formulations according to this invention such as for example milling, slow evaporation, slurry crystallization, melt crystallization, supercritical fluid crystallization. The cocrystals according to this invention are preferably manufactured by milling. Two major techniques for milling in general exist: dry milling and wet milling. In dry milling, cocrystal formers are milled together using a mortar and pestle, a ball mill, or a vibratory mill. In wet milling, a small amount of liquid (solvent) is added to the grinding mixture. In the context of the present invention the co-crystals are preferably prepared by wet milling using water as a solvent.

Nano-sized co-crystal suspensions of the present invention are stable after dilution for at least 12 to 24 h.

There are no special restrictions to the active ingredient (drugs) used in the present invention, although the invention is in particular very suitable for the poorly water-soluble drugs. In general the phrase "poorly water-soluble drug" specifically means a drug having a solubility in purified water of 0.15 mg/mL or less, preferably 0.05 mg/mL or less. The drug can be selected from a variety of known drugs, including but not limited to analgesics, anti-inflammatory drugs, anthelmintics, anti-arrhythmic agents, antibiotics (including penicillins), anticoagulants, anticoccidials, antidepressants, antidiabetic agents, antiepileptics, antihistamines, anti-hypertensive drugs, antimuscarinic agents, antimycobacterial agents, antineoplastic agents, immunosuppressants, antithyroid drugs, antiviral agents, anxiolytic drugs, anti-allergic agents, . . . ; preferably anthelmintics.

In a specific embodiment, the present invention provides a pharmaceutical suspension as defined herein, wherein the poorly water-soluble drug is an anthelmintic, in particular a benzimidazole-based anthelmintic.

The term "anthelmintic" as used herein is meant to be an anti-parasitic drug. In general anthelmintics expel parasites from the body, by either stunning or killing them. Many types of anthelmintics exist, including benzimidazole-based anthelmintics, all of these comprising a benzimidazole structure, as shown below:

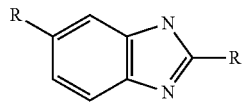

Exemplary benzimidazole-based anthelmintics suitable in the context of the present invention include albendazole, mebendazole, thiabendazole, fenbendazole, oxfendazole, febantel, triclabendazole and flubendazole; in particular flubendazole.

The term "dicarboxylic acid" as used herein is meant to include any organic compound that contains two carboxylic acid functional group, and is generally represented by the following formula HOOC—R—COOH, where R may be an alkyl, alkenyl, alkynyl or aryl group. Exemplary alkyl containing dicarboxylic acids, arranged by increasing length of the alkyl linker, include but are not limited to oxalic acid, malonic acid, succinic acid, glutaric acid, adipic acid, pimelic acid, suberic acid, azelaic acid, sebacic acid, undecanedioic acid and dodecanedioic acid. Exemplary aryl containing dicarboxylic acids include but are not limited to phthalic acid, isophthalic acid and terephthalic acid. Exemplary alkenyl containing dicarboxylic acids include but are not limited maleic acid, fumaric acid, glutaconic acid, traumatic acid and muconic acid. In a specific embodiment, the co-crystals of the present invention contain adipic acid.

In a preferred embodiment, the present invention provides a pharmaceutical suspension according to this invention comprising a surfactant and nano-sized cocrystals of flubendazole and adipic acid.

The present invention also provides a pharmaceutical composition obtained by drying the pharmaceutical suspension according to this invention. Any suitable method for drying a pharmaceutical suspension, could be applied, such as for example but not limited to spray-drying, solvent evaporation, hot air drying, drum drying, vacuum drying and freeze drying, in particular spray-drying.

The present invention further provides a pharmaceutical suspension or composition according to this invention for use as a human or veterinary medicine.

In a specific embodiment, the present invention provides the use of anthelmintic-containing suspensions and compositions according to this invention for the treatment of parasitic infections in a subject in need thereof.

As used herein "a subject" is meant to include any living being in particular selected from humans; and animals such as livestock including pigs, poultry, cattle and sheep.

The present invention further provides the use of one or more dicarboxylic acids for the manufacturing of a pharmaceutical suspension or composition according to this invention.

It further provides a method for the treatment of parasitic infections; said method comprising administering a pharmaceutical suspension or composition according to this invention to a subject in need thereof.

Examples of parasitic infections are infections with protozoa or helminths, in particular monogeneans, cestodes (tapeworms), nematodes (roundworms), and trematodes (flukes).

The present invention also provides a method for the manufacturing of a pharmaceutical suspension according to to this invention; said method comprising:
  Dispersing at least one active ingredient, at least one dicarboxylic acid, and a surfactant in water, and
  Milling said dispersion.

Finally the present invention provides a method for the manufacturing of a pharmaceutical composition according to to this invention; said method comprising:
  Dispersing at least one active ingredient, at least one dicarboxylic acid, and a surfactant in water,
  Milling said dispersion, and
  Drying the pharmaceutical suspension.

Detailed procedures for obtaining the pharmaceutical suspensions and compositions according to this invention can be found in the examples that follow hereinafter.

In general the active ingredient(s) and dicarboxylic acid(s) are dispersed in water further comprising a surfactant, however without organic solvents. It is evident for a person skilled in the art that the amount of active ingredient, surfactant and dicarboxylic acid suitable for obtaining the suspensions and compositions according to this invention depend on the type of compounds used. In general about 40/60, 45/55, 50/50, 70/30 (w/w) of active ingredient/dicarboxylic acid can be used; in particular about 40/60, e.g. 38.5/61.5.

In general about and between 0.01 and 0.2 g/ml active ingredient is used; more preferably about and between 0.01 and 0.1 g/ml; in particular about 0.05 g/ml.

In general about and between 0.01 and 0.2 g/ml dicarboxylic acid is used; more preferably about and between 0.05 and 0.1 g/ml; in particular about 0.08 g/ml.

The term "surfactant" is meant to include any compound capable of lowering the surface tension of a liquid. Suitable surfactants that can be used for preparing the suspensions and compositions according to this invention include but are not limited to SDS (sodium dodecyl sulphate), docusate, poloxamers, Triton X-100 (4-(1,1,3,3-Tetramethylbutyl)

phenyl-polyethylene glycol), Tween 20 (polysorbate 20), Tween 80 (polysorbate 80), . . . ; in particular Tween 80. The surfactant is generally used at a concentration of about and between 0.005 and 0.02 g/ml; more preferably about and between 0.010 and 0.015 g/ml; in particular about 0.0125 g/ml.

After dispersing the active ingredient, the dicarboxylic acid and the surfactant in water, the suspension is milled. Any suitable method for milling a suspension can be used as further detailed herein. In particular about and between 20-50 g of milling beads such as zirconium beads are added and the suspension is milled on a roller-mill with a speed of about and between 100-300 rpm, in particular about 150 rpm for at least 24 h, preferably at least 48 h, more preferably at least 60 h.

This invention will be better understood by reference to the Experimental Details that follow, but those skilled in the art will readily appreciate that these are only illustrative of the invention as described more fully in the claims that follow thereafter. Particular embodiments and examples are not in any way intended to limit the scope of the invention as claimed. Additionally, throughout this application, various publications are cited. The disclosure of these publications is hereby incorporated by reference into this application to describe more fully the state of the art to which this invention pertains.

EXAMPLES

Example 1: Co-Crystal Formation of Flubendazole and Adipic Acid

A. Preparation of Nano-Suspension
First:
  0.25 g Flubendazole (benzimidazole based anthelmintic),
  0.4 g adipic acid (a dicarboxylic acid), and
  0.0625 g Tween® 80 (a non-ionic tension-active agent)
were dispersed in 5 ml of demineralised water. Then, 30 g Zirconium beads (diameter 0.5 mm) were added.

Subsequently, the suspension was milled on a roller-mill with a speed set at 150 RPM. After ±60 hours an aqueous nano-suspension was obtained, said nanoparticles having a mean particle size of 304±42 nm. Furthermore, the nano-suspension was stable after dilution for at least 12 h, as evident from part B of this example.
B. System Availability
A volume of the nano-suspension obtained in part A of this example, corresponding with the therapeutic dose of flubendazole, was diluted with drinking water in a drinking water reservoir used for pigs. Samples were taken at the reservoir and at the nipples 0, 1, 2, 4, 6, 12 and 24 h after addition of the suspension to the drinking water. The concentration of flubendazole in all samples was determined. The concentration of flubendazole in the drinking water reservoir and the nipples was only decreased 10% after 12 h. After 24 h, the flubendazole concentration was decreased 15 and 45% in the reservoir and the nipples, respectively.

Example 2: Co-Crystal Formation of Flubendazole and Adipic Acid

In this further example, the preparation of example 1 was repeated, yielding a nano-suspension with nanoparticles having a mean particle size of 182±4 nm.

The nanosuspension was diluted at therapeutic dose in drinking water. Samples were taken immediately after dilution and 2, 4, 6, 8, 10, 12 and 24 h after dilution to measure the particle size in function of time. A summary of the results is given in Table 2.

TABLE 2

| Particle size in function of time | |
|---|---|
| Time Point (h) | Mean particle size ± SD (nm) |
| 0 | 182 ± 4 |
| 2 | 175 ± 5 |
| 4 | 190 ± 8 |
| 6 | 186 ± 5 |
| 8 | 193 ± 3 |
| 10 | 195 ± 2 |
| 12 | 199 ± 12 |
| 24 | 243 ± 8 |

As evident from table 2, the mean particle size of the obtained nanocrystals remains stable for at least 24 h after dilution in drinking water.

Example 3: Preparation of a Nano-Suspension with Flubendazole and Succinic Acid 0.25 g flubendazole (benzimidazole based anthelmintic), 0.4 g succinic acid (a dicarboxylic acid) and 0.0625 g Tween® 80 (a non-ionic tension-active agent) were dispersed in 5 ml of demineralised water. Then 30 g Zirconium beads (diameter 0.5 mm) were added.

Subsequently, the suspension was milled on a roller-mill with a speed set at 150 RPM. After ±60 hours an aqueous nano-suspension was obtained, said nanoparticles having a mean particle size of 207±9 nm.

Example 4: Preparation of a Nano-Suspension with Fenbendazole and Succinic Acid 0.25 g fenbendazole (benzimidazole based anthelmintic), 0.4 g succinic acid (a dicarboxylic acid) and 0.0625 g Tween® 80 (a non-ionic tension-active agent) were dispersed in 5 ml of demineralised water. Then 30 g Zirconium beads (diameter 0.5 mm) were added.

Subsequently, the suspension was milled on a roller-mill with a speed set at 150 RPM. After ±60 hours an aqueous nano-suspension was obtained, said nanoparticles having a mean particle size of 415±48 nm.

Example 5: Preparation of a Nano-Suspension with Fenbendazole and Adipic Acid 0.25 g fenbendazole (benzimidazole based anthelmintic), 0.2 g adipic acid (a dicarboxylic acid) and 0.0625 g Tween® 80 (a non-ionic tension-active agent) were dispersed in 5 ml of demineralised water. Then 30 g Zirconium beads (diameter 0.5 mm) were added.

Subsequently, the suspension was milled on a roller-mill with a speed set at 150 RPM. After ±60 hours an aqueous nano-suspension was obtained, said nanoparticles having a mean particle size of 435±22 nm.

Example 6: Preparation of a Nano-Suspension with Flubendazole and Glutaric Acid 0.25 g flubendazole (benzimidazole based anthelmintic), 0.4 g glutaric acid (a dicarboxylic acid) and 0.0625 g Tween® 80 (a non-ionic tension-active agent) were dispersed in 5 ml of demineralised water. Then 30 g Zirconium beads (diameter 0.5 mm) were added.

Subsequently, the suspension was milled on a roller-mill with a speed set at 150 RPM. After ±60 hours an aqueous nano-suspension was obtained, said nanoparticles having a mean particle size of 494±32 nm.

Example 7: Preparation of a Nano-Suspension with Fenbendazole and Maleic Acid 0.25 g flubendazole (benzimidazole based anthelmintic), 0.2 g maleic acid (a dicarboxylic acid) and 0.0625 g Tween® 80 (a non-ionic tension-active agent) were dispersed in 5 ml of demineralised water. Then 30 g Zirconium beads (diameter 0.5 mm) were added.

Subsequently, the suspension was milled on a roller-mill with a speed set at 150 RPM. After ±60 hours an aqueous nano-suspension was obtained, said nanoparticles having a mean particle size of 506±389 nm.

Example 8: Preparation of a Nano-Suspension with Fenbendazole and Glutaric Acid 0.25 g Fenbendazole (benzimidazole based anthelmintic), 0.2 g glutaric acid (a dicarboxylic acid) and 0.0625 g Tween® 80 (a non-ionic tension-active agent) were dispersed in 5 ml of demineralised water. Then 30 g Zirconium beads (diameter 0.5 mm) were added.

Subsequently, the suspension was milled on a roller-mill with a speed set at 150 RPM. After ±60 hours an aqueous nano-suspension was obtained, said nanoparticles having a mean particle size of 764±168 nm.

Example 9: Spray Drying of the Suspension 5 g Mannitol is added to a 50 ml suspension containing 700 mg flubendazole, 1.2 g adipic acid and 125 mg Tween 80.

Next the suspension is spray dried at an inlet temperature of 120° C. and an outlet temperature of 54° C.

The invention claimed is:

1. A method for manufacturing a pharmaceutical nano-suspension, said method comprising:
    (a) dispersing at least one active ingredient, at least one dicarboxylic acid, and a surfactant in water, wherein:
        (i) the at least one dicarboxylic acid is adipic acid; and
        (ii) the surfactant is polysorbate 80; and
        (iii) the at least one active ingredient is selected from the group consisting of flubendazole and fenbendazole; and
    (b) milling said dispersion,
wherein no organic solvent is used in (a) or (b).

2. The method according to claim 1, further comprising:
    (c) drying the pharmaceutical nanosuspension.

3. A pharmaceutical nanosuspension obtained by the method according to claim 1.

4. The pharmaceutical nanosuspension of claim 3, wherein the pharmaceutical nanosuspension is stable for at least 24 hours.

* * * * *